(12) United States Patent
Dhanasingh

(10) Patent No.: US 11,524,154 B2
(45) Date of Patent: Dec. 13, 2022

(54) NAVIGATABLE IMPLANTABLE ELECTRODE AND COLLAPSING LUBRICANT RESERVOIR

(71) Applicant: MED-EL Elektromedizinische Geraete GmbH, Innsbruck (AT)

(72) Inventor: Anandhan Dhanasingh, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 16/755,670

(22) PCT Filed: Nov. 9, 2018

(86) PCT No.: PCT/US2018/059937
§ 371 (c)(1),
(2) Date: Apr. 13, 2020

(87) PCT Pub. No.: WO2019/094666
PCT Pub. Date: May 16, 2019

(65) Prior Publication Data
US 2021/0187283 A1 Jun. 24, 2021

Related U.S. Application Data

(60) Provisional application No. 62/584,166, filed on Nov. 10, 2017.

(51) Int. Cl.
*A61N 1/05* (2006.01)
*A61N 1/36* (2006.01)

(52) U.S. Cl.
CPC ....... *A61N 1/0541* (2013.01); *A61N 1/36039* (2017.08)

(58) Field of Classification Search
CPC .................. A61N 1/0541; A61N 1/36039
See application file for complete search history.

(56) References Cited

U.S. PATENT DOCUMENTS 6,309,410 B1 10/2001 Kuzma et al.
2012/0245534 A1 9/2012 Jolly
(Continued)

FOREIGN PATENT DOCUMENTS

WO   WO 03/034960 A1   5/2003

OTHER PUBLICATIONS

International Searching Authority/European Patent Office, International Search Report and Written Opinion of the International Searching Authority, Application No. PCT/US2018/059937, dated Feb. 11, 2019, 13 pages.

*Primary Examiner* — Joseph M Dietrich
(74) *Attorney, Agent, or Firm* — Sunstein LLP

(57) ABSTRACT

An implantable electrode arrangement for a cochlear implant system includes an elongated electrode array for insertion into a patient cochlea. A fluid delivery channel is located within the electrode array parallel to a central longitudinal axis with at least one fluid delivery port for delivering lubricant fluid from the fluid delivery channel to the outer surface of the electrode array. The fluid delivery port and the lubricant fluid are configured to produce a lubrication region close to the outer surface of the electrode array proximal to the fluid delivery port during insertion of the electrode array into the patient cochlea so as to reduce insertion resistance at an adjacent section of lateral wall of the patient cochlea.

11 Claims, 8 Drawing Sheets

(56) References Cited

U.S. PATENT DOCUMENTS

| | | | |
|---|---|---|---|
| 2013/0079749 A1* | 3/2013 | Overstreet | A61N 1/0541 604/285 |
| 2017/0028182 A1 | 2/2017 | Jolly et al. | |

* cited by examiner

NAVIGATABLE IMPLANTABLE ELECTRODE AND COLLAPSING LUBRICANT RESERVOIR

This application is a 371 national phase entry of Patent Cooperation Treaty Application PCT/US2018/059937, filed Nov. 9, 2018, which in turn claims priority from U.S. Provisional Patent 62/584,166, filed Nov. 10, 2017, both of which are incorporated herein by reference in their entireties.

TECHNICAL FIELD

The present invention relates to medical implants, and more specifically to an implantable electrode arrangement for cochlear implant systems.

BACKGROUND ART

A normal ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

The electrode array 110 contains multiple electrode wires embedded in a soft silicone body referred to as the electrode carrier. The electrode array 110 needs to be mechanically robust, and yet flexible and of small size to be inserted into the cochlea 104. The material of the electrode array 110 needs to be soft and flexible in order to minimize trauma to neural structures of the cochlea 104. But an electrode array 110 that is too floppy tends to buckle too easily so that the electrode array 110 cannot be inserted into the cochlea 104 up to the desired insertion depth. A trade-off needs to be made between a certain stiffness of the electrode array 110 which allows insertion into the cochlea 104 up to the desired insertion depth without the array buckling, and certain flexibility of the electrode array 110 which keeps mechanical forces on the structures of the scala tympani of the cochlea 104 low enough.

Damage and trauma cause bleeding, inflammation, perforation of soft tissue, tears and holes into membranes, and fracture of thin osseous structures. The resulting damage to the inner ear, for example, may cause loss of surviving hair cells, retrograde degeneration of the dendrite which innervates the organ of *Corti*, and in the worst case, spiral ganglion cell death in the Rosenthal's canal. Cell death means quantitatively less neural tissue is available for stimulation, and qualitatively, that less frequency-tuned fibers are available to represent frequency information.

Cochlear implant electrode array designs and surgical techniques attempt to minimize the trauma of implantation surgery so that the insertion of the electrode array into the cochlea may be as smooth and resistance free as possible, both at the apical tip and elsewhere on the outer surface of the electrode array. In some cases, there may be resistance during the electrode insertion. For example, FIG. 2 shows a cross-sectional view of a cochlea 104 during insertion of the electrode array 110 through an electrode opening 201 wherein the apical tip 202 contacts the outer lateral wall 203 at the first turn. When that occurs, the surgeon either stops the insertion with only a partial length of the electrode array 110 inside the cochlea 104, or the surgeon increases the insertion force to push the electrode array 110 beyond the resistance point, creating trauma inside the cochlea 104.

The size and mechanical characteristics of the electrode array are critical parameters for the best patient benefit. Some electrode array designs are pre-curved, though a drawback of that approach is that a special electrode insertion tool is needed which keeps the electrode array straight until the point of insertion. As documented by Erixon et al., *Variational Anatomy of the Human Cochlea: Implications for Cochlear Implantation*, Otology & Neurotology, 2008 (incorporated herein by reference), the size, shape, and curvature of the cochlea varies greatly between individuals, meaning that a cochlear implant electrode array must match a wide range of scala tympani (ST) geometries. Furthermore, recently published research by Verbist et al., *Anatomic Considerations of Cochlear Morphology and Its Implications for Insertion Trauma in Cochlear Implant Surgery*, Otology & Neurotology, 2009 (incorporated herein by reference) has shown that the human ST does not incline towards the helicotrema at a constant rate, but rather there are several sections along the ST where the slope changes, sometimes even becoming negative (i.e. downwards). The location and grade of these changes in inclination were also found to be different from individual to individual. Consequently, CI electrode arrays should be highly flexible in all directions in order to adapt to individual variations in curvature and changes in inclination of the ST for minimal trauma implantation.

It is known to provide a fluid delivery channel within the electrode array to deliver therapeutic drugs and/or insertion lubricants to the outer surface of the electrode array. For example, one such arrangement is described in U.S. Patent Publication 2017/0028182 (incorporated herein by reference in its entirety).

SUMMARY OF THE INVENTION

Embodiments of the present invention are directed to an implantable electrode arrangement for a cochlear implant system. An elongated electrode array is configured for insertion into a patient cochlea. The electrode array has a central longitudinal axis and an outer surface with multiple simulation contacts for delivering electrical stimulation signals to adjacent cochlear neural tissue. A fluid delivery channel is located within the electrode array parallel to the central longitudinal axis and has at least one fluid delivery port for delivering lubricant fluid from the fluid delivery channel to the outer surface of the electrode array. The fluid delivery port and the lubricant fluid are configured to produce a lubrication region close to the outer surface of the electrode array proximal to the fluid delivery port during insertion of the electrode array into the patient cochlea so as to reduce insertion resistance at an adjacent section of lateral wall of the patient cochlea.

In further specific embodiments, the lubricant fluid may be characterized by forming a solid lubrication region between the electrode array and the lateral wall when contacting perilymph fluid within the patient cochlea. The electrode array may include an apical end containing the least one fluid delivery port. The outer surface of the electrode array may have an outer lateral side containing the at least one fluid delivery port. The at least one fluid delivery port may be multiple fluid delivery ports or a single fluid delivery port.

There may be at least one fluid reservoir connected to the fluid delivery channel and containing the lubricant fluid, wherein the at least one fluid reservoir is configured for non-reversible collapse under compression pressure for delivery of the lubricant fluid through the at least one fluid delivery port without developing back suction into the fluid delivery channel. The at least one fluid reservoir may include a metal layer configured for the non-reversible collapse. The at least one fluid reservoir may be multiple fluid reservoirs or a single fluid reservoir.

DETAILED DESCRIPTION OF SPECIFIC EMBODIMENTS

Embodiments of the present invention are directed to an implantable electrode arrangement for a cochlear implant system with an electrode array that contains a fluid delivery channel and one or more fluid delivery ports. The fluid delivery port and the lubricant fluid are configured to produce a lubrication region on the outer surface of the electrode array proximal to the fluid delivery port during insertion of the electrode array into the patient cochlea so as to reduce insertion resistance at an adjacent section of lateral wall of the patient cochlea. It further may avoid that the electrode may touch the delicate structure of the lateral wall during insertion.

Figure 1:
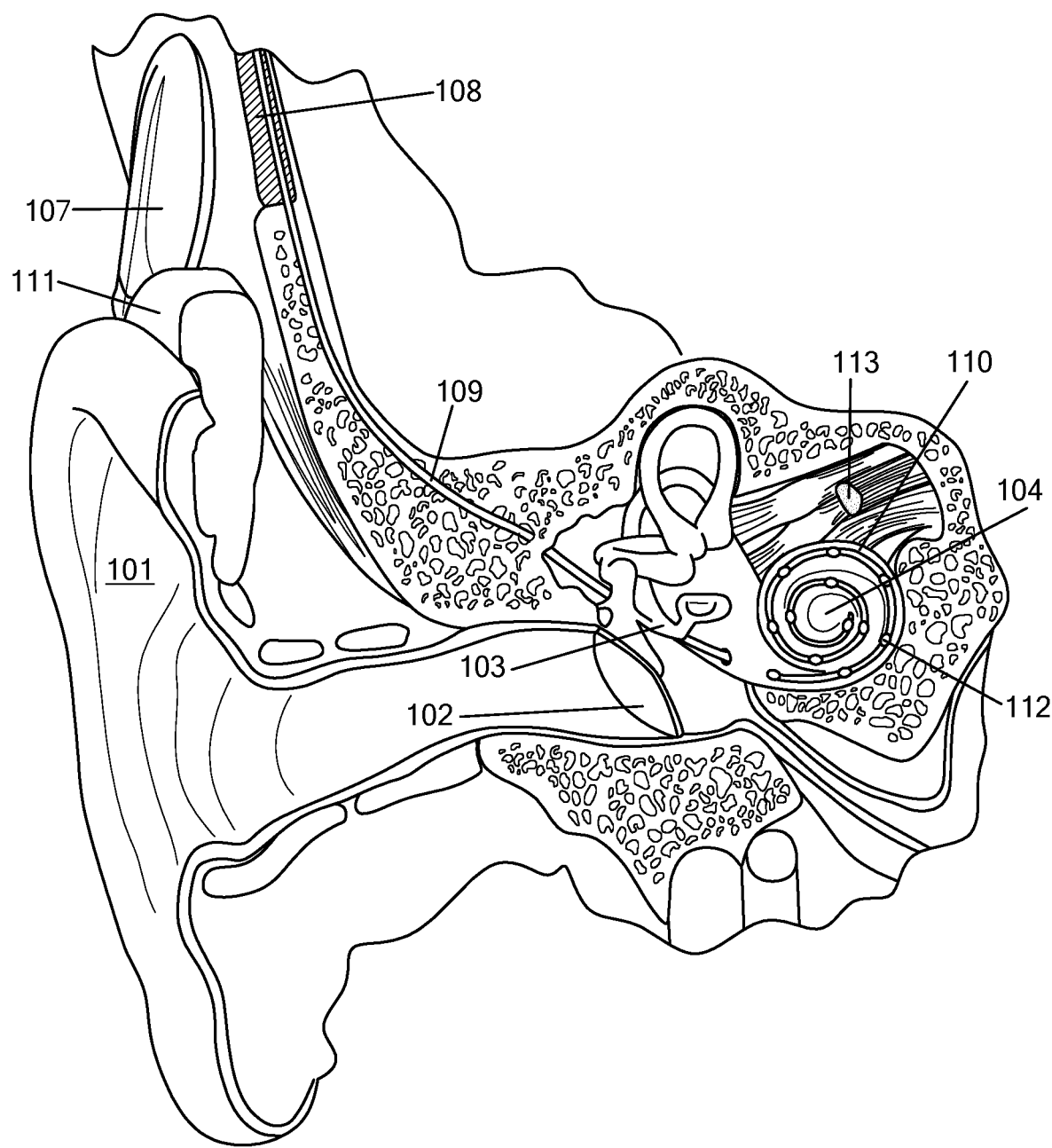
FIG. 1 shows various structures in a human ear with a cochlear implant.
Figure 2:
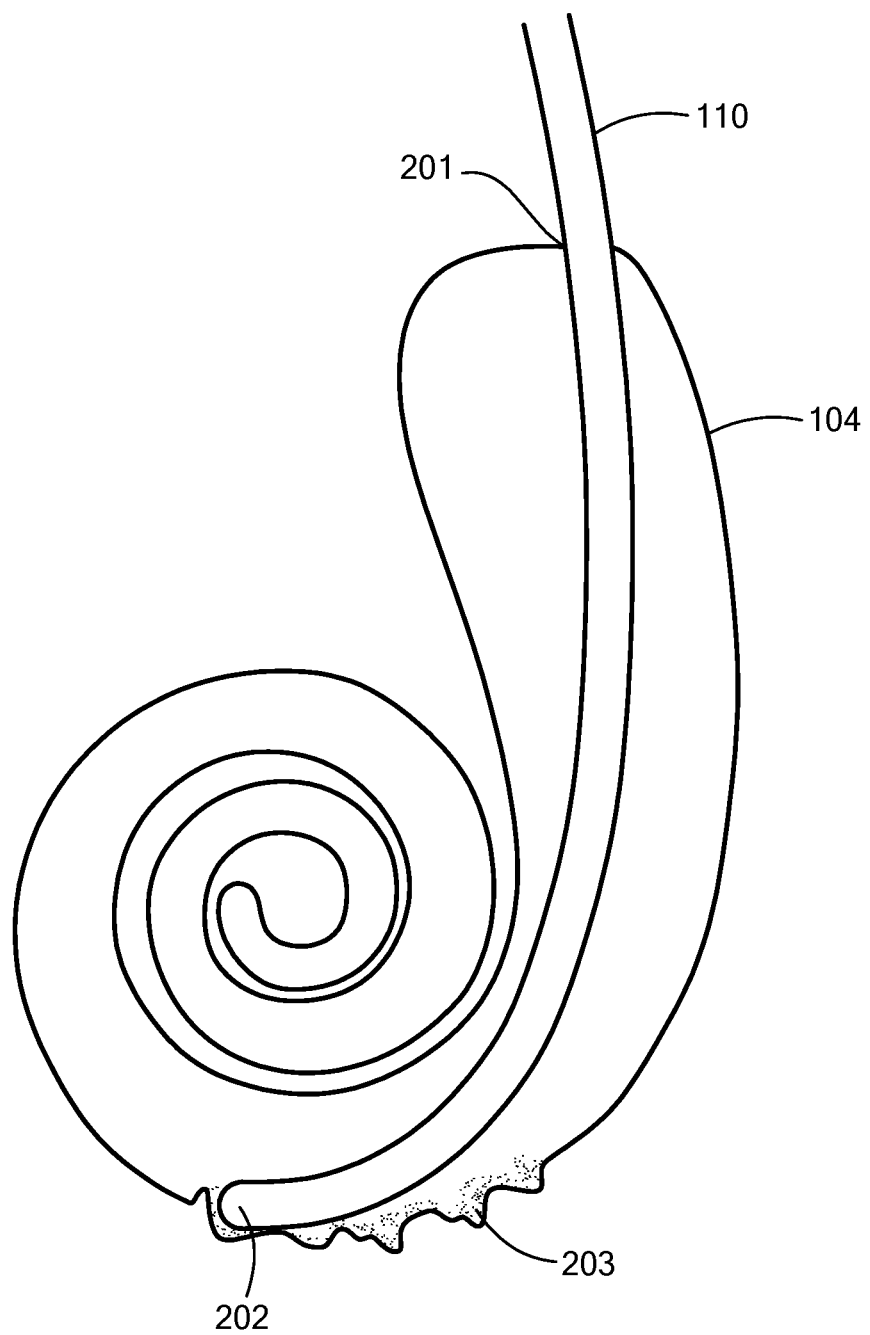
FIG. 2 shows a cross-sectional view of insertion of an electrode into a patient cochlea.
Figure 3A:
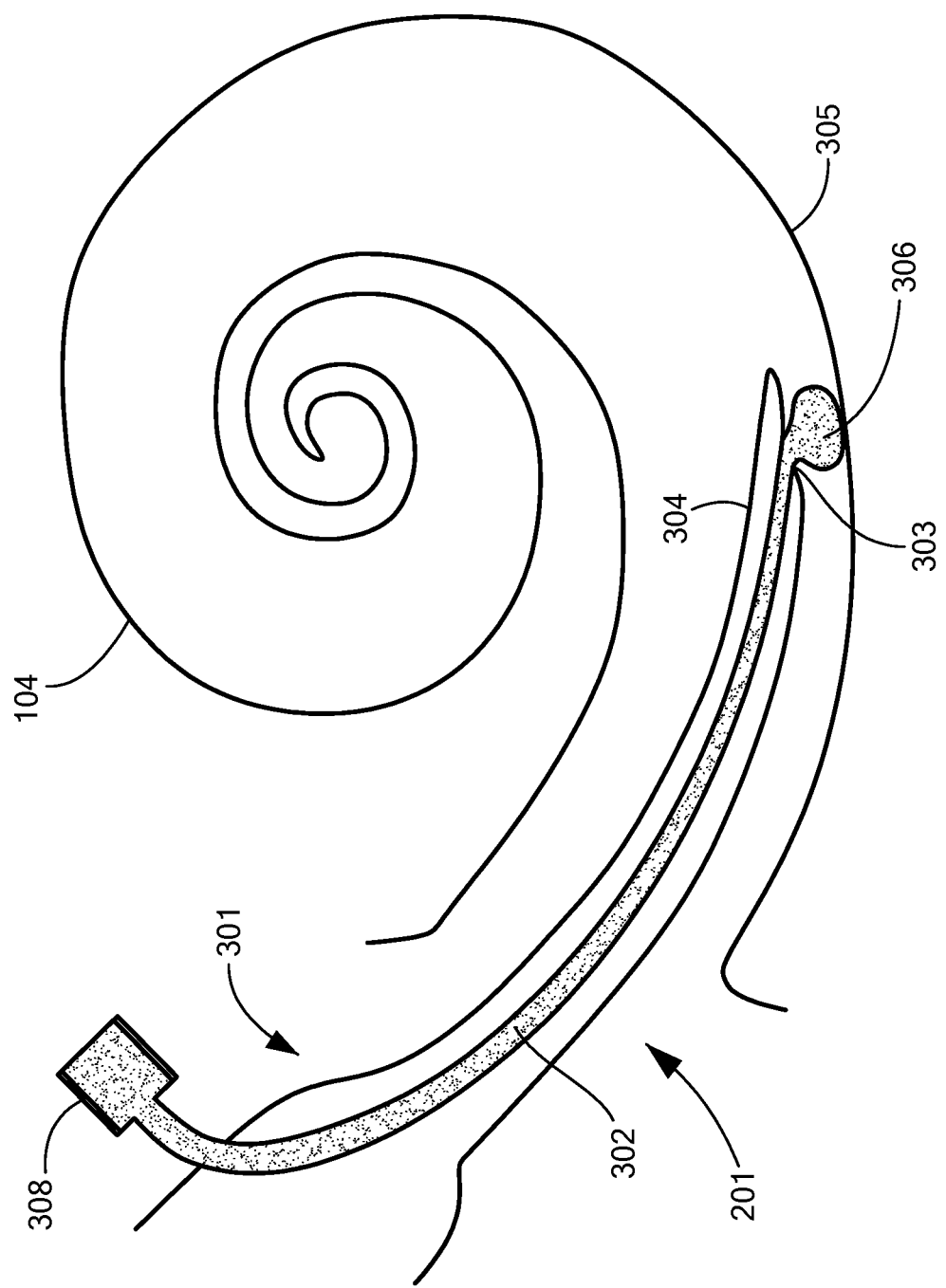
FIGS. 3A-3C show cross-sectional views of a cochlear implant electrode with a fluid delivery arrangement according to an embodiment of the present invention.
Figure 3B:
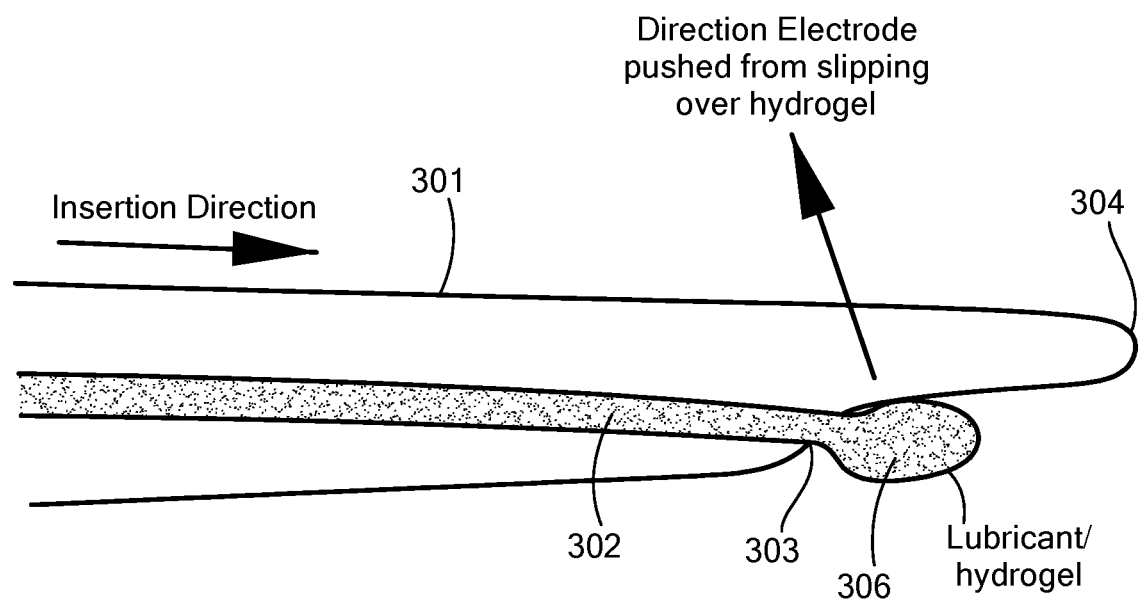
Figure 3C:
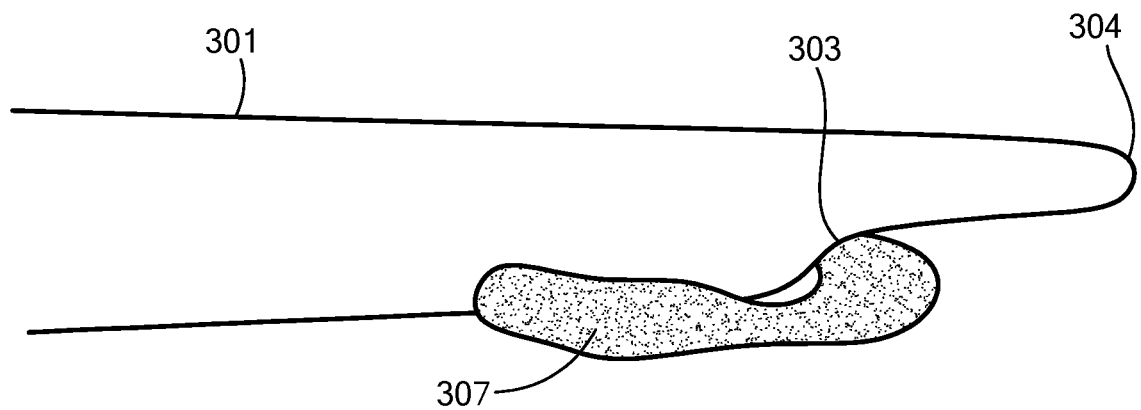

FIGS. 3A-3C show cross-sectional views of an elongated cochlear implant electrode array 301 according to an embodiment of the present invention for insertion into a patient cochlea 104. A fluid delivery channel 302 is located within the electrode array 302 and has a fluid delivery port 303 at an outer lateral side of the apical end 304 of the electrode array 301 for delivering lubricant fluid 306 from the fluid delivery channel 302 to the outer surface of the electrode array 301. That produces a lubrication region 307 close to the outer surface of the electrode array 301 proximal to the fluid delivery port 303 during insertion of the electrode array 301 into the patient cochlea 104 so as to reduce insertion resistance at an adjacent section of lateral wall 305 of the patient cochlea 104. The lubricant fluid 306 may be, a biocompatible lubricant selected from hyaluronic acid or biocompatible polyethylene glycol-based lubricants with special end groups that readily react with perilymph liquid to form a solidified hydrogel that is resorbable over time. In the embodiment shown in FIG. 3C, the fluid delivery port 303 on the apical end 304 of the electrode array 302 is adapted to release lubricant in such a way that a solid sliding groove lubrication region 307 between the electrode array 301 and the lateral wall 305 when contacting perilymph fluid within the patient cochlea 104 is formed. In this configuration, the fluid delivery port 303 may comprise two or more openings for fluid delivery, laterally separated on the outer surface of the electrode array 301. The openings may have a relative to each other varying cross-section for controlling fluid flow resistance and fluid-delivery between the openings. The electrode array 301 may slide over the solid sliding groove during insertion and thereby supports holding the electrode array 302 over the solid lubricant region 307 so as to "curl" or "navigate" the electrode during insertion in the scala tympany and avoids touching the delicate structures, for example, at the lateral wall 305.

In the embodiment shown in FIG. 3B the apical end 304 of the electrode array 302 is formed to support curling up the electrode during insertion. The apical end 304 has a tapering conical design towards the electrode array tip. The tapering may be equally around the lateral outer surface of the electrode array 302 (not shown) and/or linear along the longitudinal direction of the electrode array 302. In another embodiment, the tapering may be non-linear along the longitudinal direction of the electrode array 302 and more pronounced offset back the longitudinal direction from the electrode array tip and at or slightly after the fluid delivery port 303. The pronounced tapering may be located only at the lateral position on the electrode array 301 where a fluid delivery port 303 is arranged. With such an electrode design, while releasing lubricant fluid through the fluid delivery port 303 will form a lubricant region 307 partly in front (as seen from insertion direction) of the electrode array 302. During subsequent insertion into the scala tympany, the electrode array 302 slides over the solidified lubricant. Due to the conical tapering design of the apical end 304 and the lubricant region 307 in front of the electrode array 30, this bends or curls the electrode array 302 away from the otherwise straight insertion direction. This avoids touching the delicate structures, such as for example the lateral wall 305. The fluid delivery port 303 may be adapted in the same way as described before in relation to FIG. 3B.

It is understood by those skilled in the art, that any fluid delivery system may be used to exercise the inventive electrode arrangement as described before. In one preferable exemplary embodiment, a fluid reservoir 308 is connected to the fluid delivery channel 302 and contains a supply of the lubricant fluid 306. During surgical insertion of the electrode array 301 into a patient cochlea 104, if insertion resistance develops, the surgeon can provide squeeze the fluid reservoir 308 to develop compression pressure that pushes the lubricant fluid 306 through the fluid delivery channel 302 and out the open fluid delivery port 303 to form a lubrication region 307 that lubricates the outer surface of the electrode array 301 to overcome the resistance. The fluid reservoir 308 non-reversibly collapses under the compression pressure without returning to its original shape. For example, the fluid reservoir 308 may have a metal layer so that it collapses under compression pressure without returning to its original shape. This prevents back suction from developing that would tend to undesirably suck the fluid/perilymph mixture back into the fluid delivery channel 302. In addition to the lubricant, the reservoir/channel/port arrangement also could provide a therapeutic pharmaceutical fluid to the outer surface of the electrode array 301.

Figure 4A:
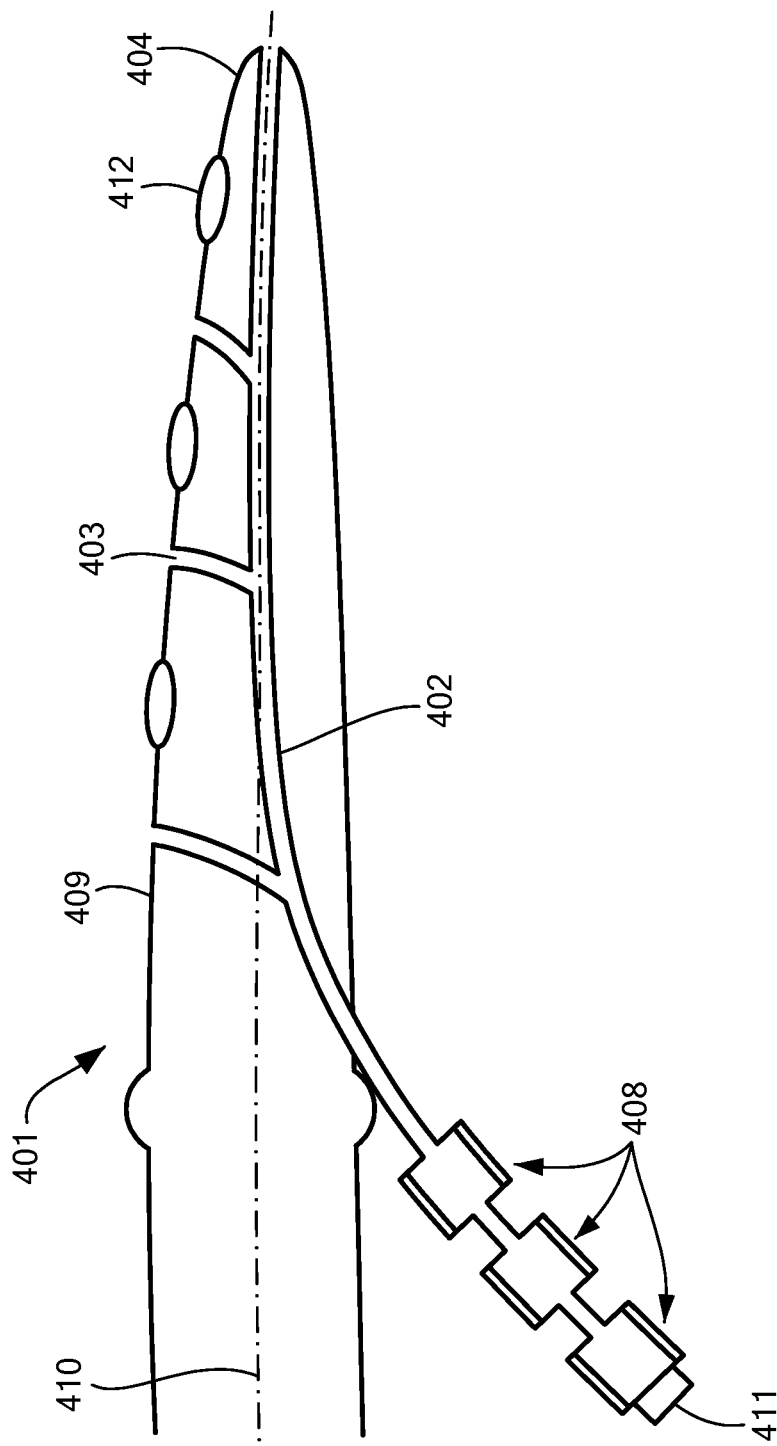
FIGS. 4A-4B show cross-sectional views of insertion of a cochlear implant electrode with a fluid delivery arrangement according to another embodiment of the present invention.
Figure 4B:
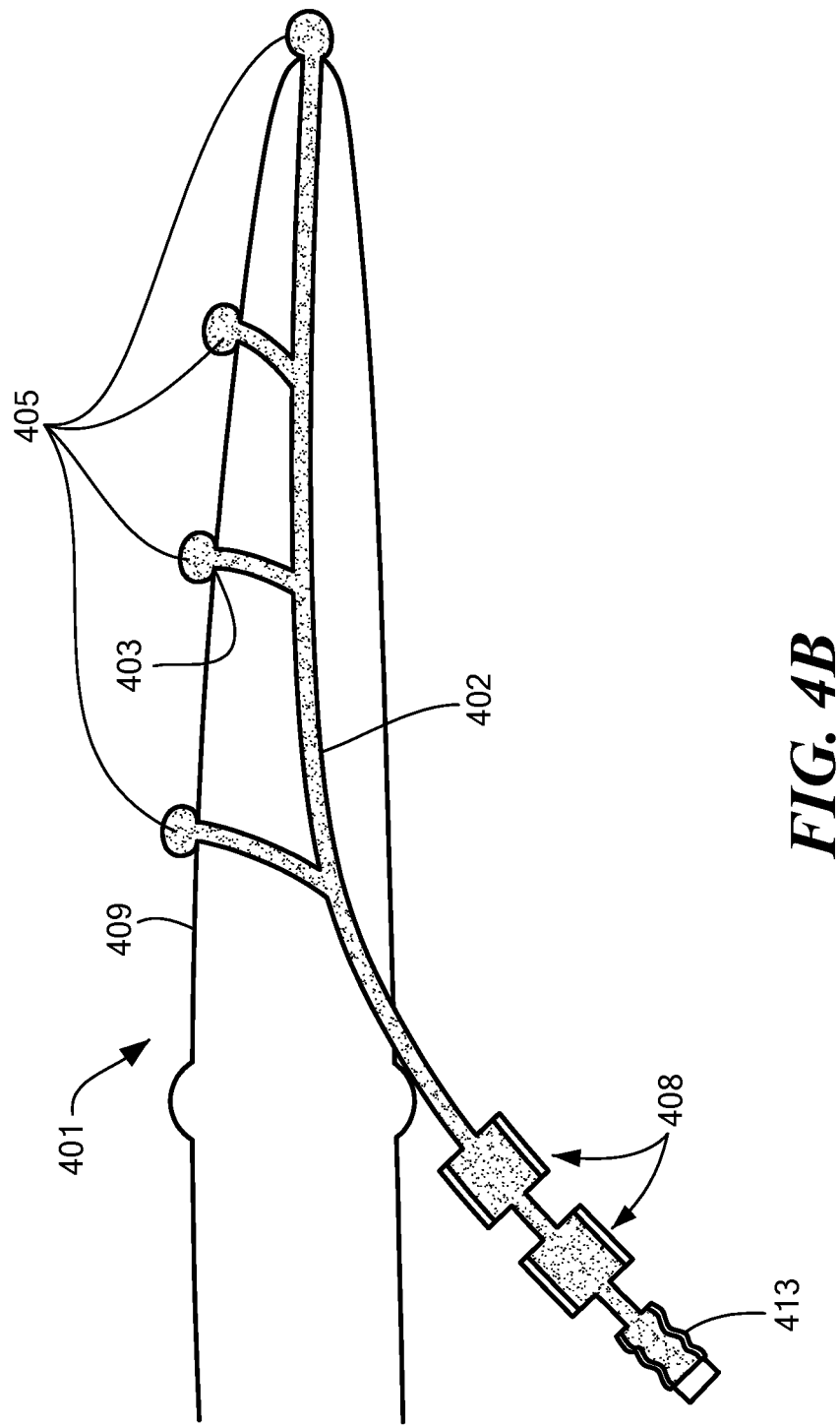

FIGS. 4A-4B show cross-sectional views of insertion of a cochlear implant electrode with a fluid delivery arrangement according to another embodiment of the present invention with multiple fluid delivery ports and multiple fluid reservoirs. An elongated electrode array 401 is configured for insertion into a patient cochlea 104. The electrode array 401 has a central longitudinal axis 410 and an outer surface 409 with multiple simulation contacts 412 for delivering electrical stimulation signals to adjacent cochlear neural tissue.

Multiple fluid reservoirs 408 are connected in series to the fluid delivery channel 402 and contain the lubricant fluid 405. The end fluid reservoir 413 has a relatively thick silicone septum 411 which can be pierced by a syringe needle for filling the fluid reservoirs 408 and the fluid delivery channel 402 with the lubricant fluid.

A fluid delivery channel 402 is located within the electrode array 401 parallel to the central longitudinal axis 410 and multiple fluid delivery ports 403 on an outer lateral surface of the outer surface 409 for delivering lubricant fluid 405 from the fluid delivery channel 402 to the outer surface 409 of the electrode array 401. The fluid delivery ports 403 and the lubricant fluid 405 are configured to produce a lubrication region on the outer surface 406 of the electrode array 401 proximal to the fluid delivery ports 403 during insertion of the electrode array 401 into the patient cochlea 104 so as to reduce insertion resistance at an adjacent section of lateral wall of the patient cochlea 104; for example, near the apical end 404 of the electrode array 401.

Figure 5A:
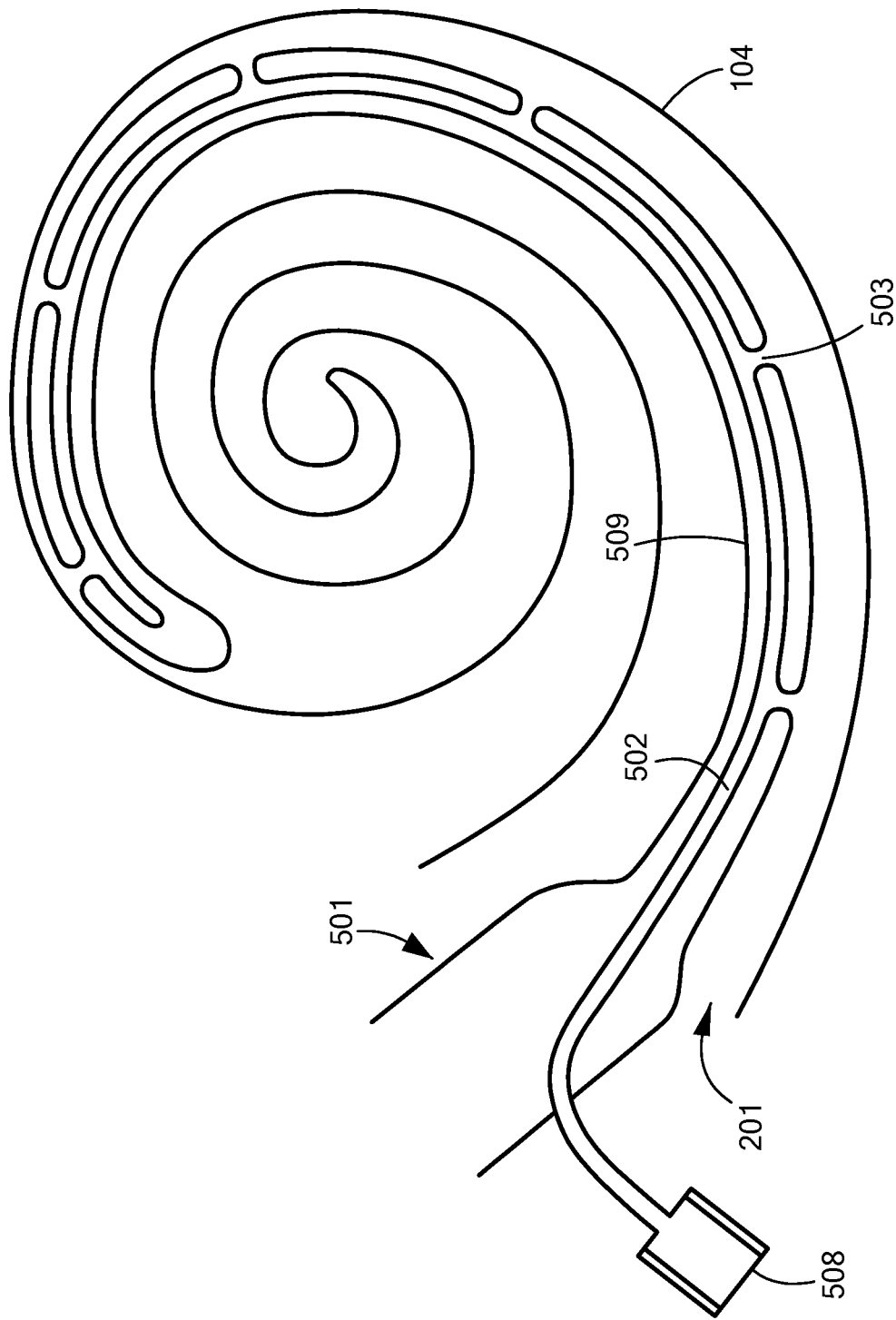
FIGS. 5A-5B show cross-sectional views of a cochlear implant electrode with a fluid delivery arrangement according to another embodiment of the present invention.
Figure 5B:
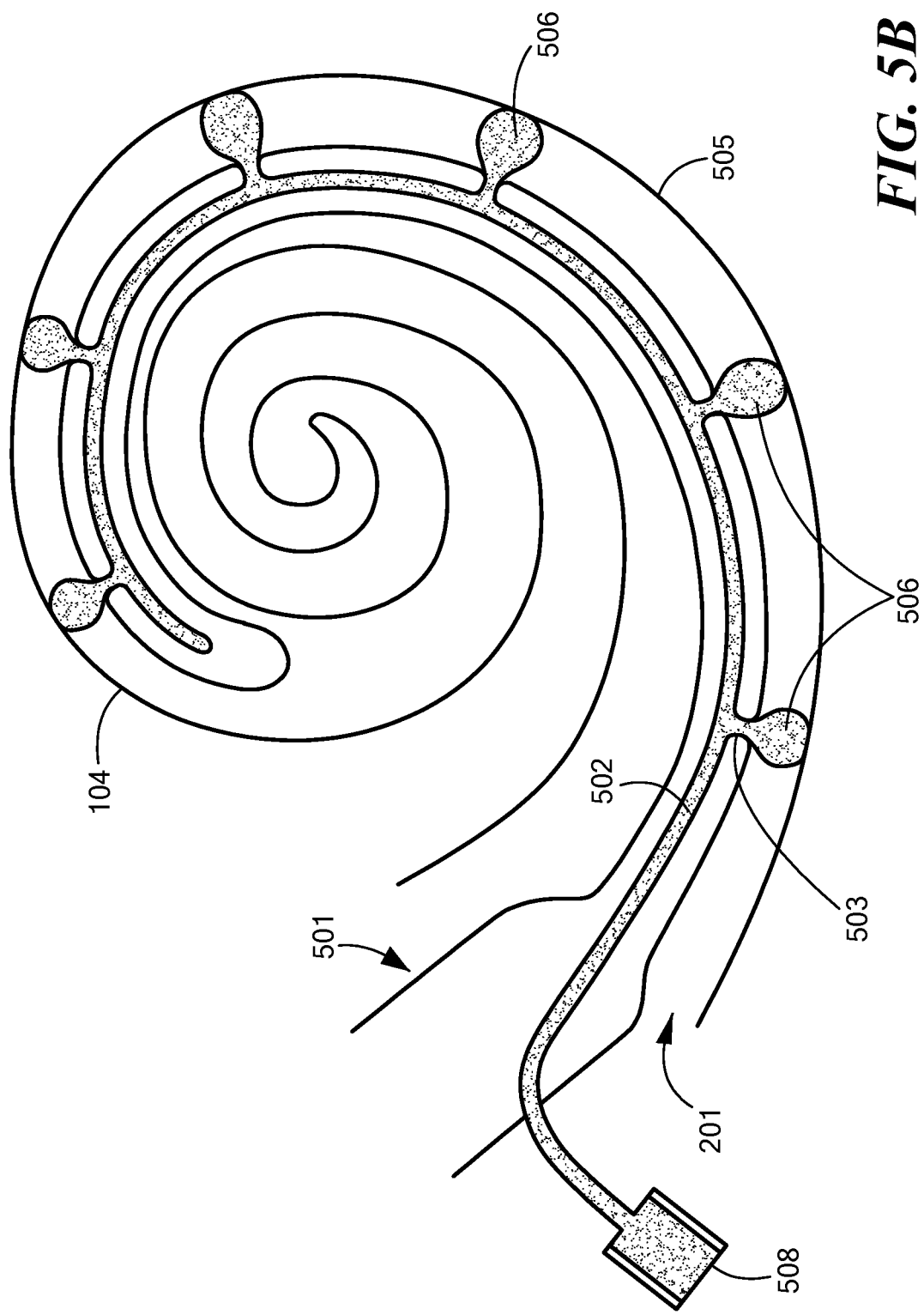

FIGS. 5A-5B show cross-sectional views of a cochlear implant electrode array 501 with a fluid delivery arrangement according to another embodiment of the present invention using one fluid reservoir 508 and multiple fluid delivery ports 503. Insertion of the electrode array 501 may be controlled during robotic surgery where the insertion depth is continuously measured and the controller of the surgical robot injects lubricant fluid 506 in the appropriate amount and time to lubricate the electrode array 501 where it contacts the lateral wall 505 of the cochlea 104.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. An implantable electrode arrangement for a cochlear implant system comprising:
    an elongated electrode array configured for insertion into a patient cochlea, the electrode array having a central longitudinal axis, an outer surface with a plurality of stimulation contacts configured for delivering electrical stimulation signals to adjacent cochlear neural tissue, and an apical end that tapers along a longitudinal direction towards a tip of the electrode array;
    a fluid delivery channel within the electrode array parallel to the central longitudinal axis and having at least one fluid delivery port configured for delivering lubricant fluid from the fluid delivery channel to the outer surface of the electrode array;
    wherein one of the fluid delivery ports is located within the apical end of the electrode array at an outer lateral position such that the one fluid delivery port and the lubricant fluid are configured to produce a lubrication region close to the outer surface of the electrode array proximal to the fluid delivery port during insertion of the electrode array into the patient cochlea so as to reduce insertion resistance at an adjacent section of lateral wall of the patient cochlea; and
    wherein the lubricant fluid is configured to react with perilymph fluid within the patient cochlea in order to form a solidified hydrogel between the electrode array and the lateral wall during the insertion.

2. An implantable electrode arrangement according to claim 1, wherein the at least one fluid delivery port is a plurality of fluid delivery ports.

3. An implantable electrode arrangement according to claim 1, wherein the at least one fluid delivery port is a single fluid delivery port.

4. An implantable electrode arrangement according to claim 1, further comprising:
    at least one fluid reservoir connected to the fluid delivery channel and containing the lubricant fluid, wherein the at least one fluid reservoir is configured for non-reversible collapse under compression pressure for delivery of the lubricant fluid through the at least one fluid delivery port without developing back suction into the fluid delivery channel.

5. An implantable electrode arrangement according to claim 4, wherein the at least one fluid reservoir includes a metal layer configured for the non-reversible collapse.

6. An implantable electrode arrangement according to claim 4, wherein the at least one fluid reservoir is a plurality of fluid reservoirs.

7. An implantable electrode arrangement according to claim 4, wherein the at least one fluid reservoir is a single fluid reservoir.

8. An implantable electrode arrangement according to claim 1, wherein the apical end tapers linearly along the longitudinal direction of the electrode array.

9. An implantable electrode arrangement according to claim 1, wherein the apical end tapers non-linearly along the longitudinal direction of the electrode array.

10. An implantable electrode arrangement according to claim 9, wherein the apical end includes an offset and the one fluid delivery port is located at the offset.

11. An implantable electrode arrangement according to claim 9, wherein the apical end includes an offset and the one fluid delivery port is located between the offset and the tip.

\* \* \* \* \*